United States Patent [19]

Okubara et al.

[11] Patent Number: 4,670,399

[45] Date of Patent: Jun. 2, 1987

[54] HYBRID PLASMID WITH MARKER

[75] Inventors: Patricia A. Okubara; Dorothy A. Pierce; Robert C. Nutter, all of Richmond, Calif.

[73] Assignee: Stauffer Chemical Co., Westport, Conn.

[21] Appl. No.: 518,222

[22] Filed: Aug. 18, 1983

Related U.S. Application Data

[63] Continuation-in-part of Ser. No. 462,731, Jan. 31, 1983, abandoned.

[51] Int. Cl.$^4$ .................... C12N 1/00; C12N 15/00
[52] U.S. Cl. .................. 435/317; 435/172.3; 935/27; 935/29; 935/30; 935/41
[58] Field of Search .................... 435/91, 172.3, 172, 435/317; 935/9, 30, 34, 27, 29, 41

[56] References Cited

U.S. PATENT DOCUMENTS 4,387,162  6/1983  Aigle et al. ............... 435/317 X
4,399,216  8/1983  Axel et al. ................ 435/317 X

FOREIGN PATENT DOCUMENTS 0068740  6/1982  European Pat. Off. ........ 435/172.3
2489364  8/1980  France ..................... 435/172.3

OTHER PUBLICATIONS

Leemans et al., *The EMBO Journal*, vol. 1, No. 1, pp. 147–152, 1982.
McPherson, *Nuc Acids Res*, vol. 12(5), pp. 2317–2325, 1984.
Sciaky, D. et al., *Nuc Acids Res.*, vol. 12(3), pp. 1447–1461, 1984.
Depicker, A. et al., *J. Molec and Applied Genetics*, vol. 1, pp. 361–370, 1982.
Broach, J. R., et al., *Gene* 8: 121–133, 1979.
O'Hare, K. et al., *PNAS* 78, No. 3: 1527–1531, 1981.
Lusty, C. J. et al., *PNAS*, 79: 2240–2244, 1982.
Fling, M. E. et al., *J. of Bact*, vol. 141, No. 2, pp. 779–785, 1980.
McKnight, T. D. et al., *J. of Cellular Biochemistry Supp.* 7, Part B, p. 268, May 13, 1983.
Simpson, R. B. et al., Cell, vol. 29, pp. 1005–1015, Jul. 1982.
Klee, H. J. et al., *J. of Bact*, vol. 150, No. 1: pp. 327–331, Apr. 1982.
Chilton, M. et al., Stadler Symposium, vol. 13: 39–52.
Kemp, J. D., Experimental Manipulation of Gene Expression, pp. 119–135, Academic Press, Inc., 1983.
"The TL—DNA in Octopine Crown—Gall Tumours Codes for Several Well—Defined Polyadenylated Transcripts", Willmitzer et al., *The EBMO Journal*, vol. 1, No. 1, pp. 139–148, (1982).
"Identification of Sequences Involved in the Polyadenylation of Higher Plant Nuclear Transcripts Using Agrobacterium T—DNA Genes as Models", Dhaese et al., *The EBMO Journal*, vol. 2, No. 3, pp. 419–426, 1983.

*Primary Examiner*—Thomas G. Wiseman
*Assistant Examiner*—Jayme A. Huleatt
*Attorney, Agent, or Firm*—Michael J. Bradley; Leona L. Lauder; Elliott L. Fineman

[57] ABSTRACT

Recombinant plasmids adopted for transformation of prokaryotic and eukaryotic hosts having an insertion site for at least one DNA fragment are provided. In a preferred embodiment, nucleotide sequences coding for methotrexate-resistant dihydrofolate reductase and a nucleotide sequence, a portion thereof coding for a promoter, are ligated into the insertion site.

10 Claims, 9 Drawing Figures

HYBRID PLASMID WITH MARKER

CROSS REFERENCE TO RELATED APPLICATION

This application is a continuation-in-part of U.S. patent application Ser. No. 462,731, filed Jan. 31, 1983 now abandoned.

BACKGROUND OF THE INVENTION

It is well known that the frequency of transformation of a cell, whether prokaryotic, for example *Escherichia coli l (E. coli)*, or eukaryotic, for example *Saccharomyces cerevisiae (S. cerevisiae)*, by plasmids is relatively small. Thus, it is desirable to include, within the genome of the transforming plasmid, certain characteristics which may be used to identify transformed cells. Such identification characteristics are known within the art as markers and may include specific nucleotide sequences, drug resistance, including antibiotic resistance, characteristics, or the ability to synthesize specific growth factors, for example amino acids, which the non-transformed host cell cannot otherwise synthesize.

SUMMARY AND OBJECTS OF THE INVENTION

The present invention concerns a plasmid-carried transformation marker which is suitable for indicating transformation in both prokaryotic and eukaryotic transformants. In addition, the invention concerns the creation of a particular insertion site on this plasmid for deoxyribonucleic acid (DNA) sequences which are to be replicated within eukaryotic or prokaryotic transformants. More particularly, new plasmids having therein a nucleotide sequence coding for methotrexate resistant dihydrofolate reductase (Mtx$^r$ DHFR) therein are synthesized. This nucleotide sequence is ligated into a doubly digested plasmid vector, YEp13, a hybrid plasmid having initial selectable markers for ampicillin and tetracycline resistance and genome regions derived from *S. cerevisiae* and *E. coli*. In a preferred embodiment, the site of insertion of the nucleotide sequence coding for Mtx$^r$ DHFR is on one end contiguous with the yeast portion of the plasmid vector downstream of a portion of the yeast portion of the plasmid vector known to contain therein a eukaryotic origin-replicator region and on the other end is contiguous with the bacterial portion of the plasmid and upstream of a portion of the bacterial portion known to contain therein a prokaryotic origin-replicator region. In another embodiment, an additional nucleotide sequence known to include a promoter therein may also be inserted downstream of the eukaryotic origin-replicator region to form another new plasmid. The plasmids have been cloned into *E. coli* strain LE392. Plasmid MTX4, cloned into *E. coli* strain LE392, has been deposited under ATCC 39276. Plasmid MTX5, cloned into E. coli strain LE392, has been deposited under ATCC 39275. Plasmid MTX4/4269, cloned into *E. coli* strain LE392 has been deposited under ATCC 39395. MTX5/4269C has been cloned into *E. coli* strain LE392 and has been deposited under ATCC 39394.

The above-mentioned plasmids, cloned into *E. coli* strain LE392 are deposited with the American Type Culture Collection, located in Rockville, Md. USA. The above-mentioned plasmids are also deposited pursuant to the requirements of foreign patent laws of countries in which counterparts of the subject application have been filed. The deposit of the above-mentioned plasmids does not in itself constitute a license to practice the subject invention in derogation of patent or certificate of invention rights granted the Assignee, the Stauffer Chemical Company by any governmental action.

The process by which these plasmids are synthesized is also described and may be briefly summarized as follows: YEp13 plasmids are exhaustively and specifically digested using BamHI and HindIII restriction endonuclease (hereinafter referred to as restrictase). The nucleotide sequence coding for Mtx$^r$ DHFR is isolated from plasmid pFE364 and prepared for ligation with octanucleotide linkers, the nucleotide sequence coding for Mtx$^r$ DHFR is ligated into prepared YEp13 fragments to yield a number of new plasmids including MTX4 and MTX5, both being hybrid plasmids having therein a nucleotide sequence cooding for Mtx$^r$ DHFR therein. The term "hybrid" as used herein means comprised of DNA from more than one source, and being capable of replication in both eukaryotic and prokaryotic cells.

The synthesis of plasmids containing an additional nucleotide sequence known to include a plant promoter therein by be briefly described as follows: MTX4 plasmids are specifically digested with HindIII restrictase. A nucleotide sequence having approximately 480 base pairs, hereinafter referred to as the 480-base pair fragment, is excised from plasmid pR4269 using HindIII and Bam HI restrictases. This nucleotide sequence is prepared for ligation with octanucleotide linkers after which it is ligated into the MTX4 or MTX5 plasmid to yield hybrid plasmids containing both the nucleotide sequence coding for Mtx$^4$ DHFR and the 480-base pair fragment containing the plant promoter.

It is an object of the invention to synthesize a hybrid plasmid having therein a marker nucleotide sequence.

It is another object of the invention to synthesize a hybrid plasmid which has therein a nucleotide sequence coding for methotrexate-resistant dihydrofolate reductase therein.

It is a further object of the invention to synthesize a plasmid which has therein a nucleotide sequence coding for a eukaryotic promoter and nucleotide sequence coding for a marker.

It is still another object of the invention to synthesize a plasmid which has therein a nucleotide sequence coding for a plant promoter and a nucletotide sequence coding for a marker.

It is a further object of the invention to synthesize a plasmid which increases the resistance to methotrexate of prokaryotic and eukaryotic organisms transformed by the plasmid.

It is still another object of the invention to synthesize a plasmid which produces methotrexate-resistant dihydrofolate reductase in prokaryotic and eukaryotic organisms containing the plasmid.

BRIEF DESCRIPTION OF THE DRAWINGS

These and other objects of the invention will be apparent to those skilled in the art from the following description of the drawings in which.

DETAILED DESCRIPTION AND PREFERRED EMBODIMENTS

EXAMPLE I

Figure 1:
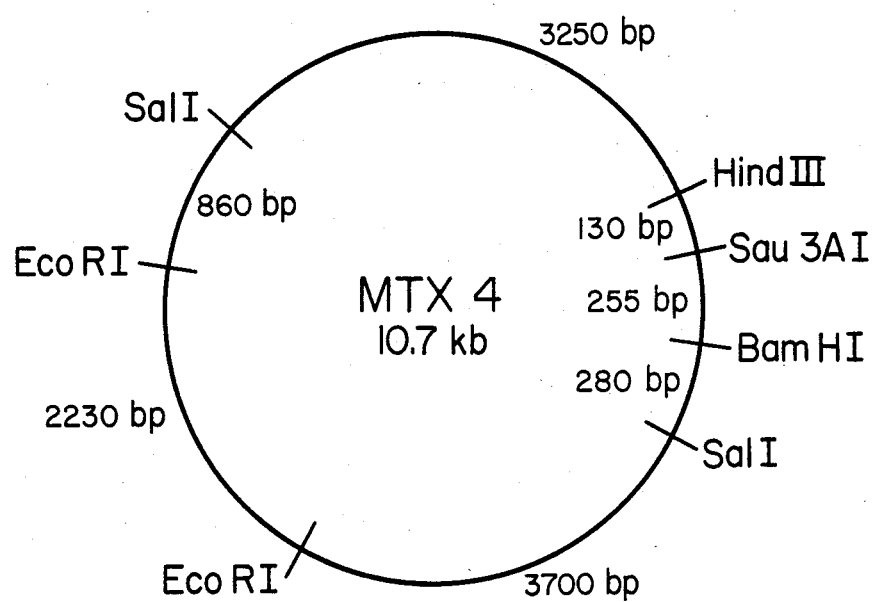
FIG. 1 is a schematic restriction map of MTX4 plasmid having therein a nucleotide sequence coding for Mtx$^r$ DHFR therein.

Preparation of Hybrid Plasmids Carrying Mtx$^r$ DHFR

The following examples are intended to be exemplary and are not intended to be limiting. It will be readily apparent to those skilled in the art that the various steps described hereinbelow may be varied without departing from the essence of the invention described. For example, buffer strengths, centrifugation rates and times, extractions, precipitations, washes and the like can be varied within limits without changing the essence of the invention described. Equally nucleotide linkers, enzymes and commercial sources for the same can be varied without departing from the essence of the invention herein described.

YEp13 plasmid was obtained from V. Williamson, University of Washington, Seattle, Washington. YEp13 has been described by Broach, Strathern and Hicks in (1979) *Gene*, Vol. 8, 121-133. YEp13 plasmid is a hybrid and has a yeast DNA region derived from the eukaryotic microorganism *S. cerevisiae*. Within the yeast DNA region is a eukaryotic origin-replicator region. YEp13 also has a bacterial DNA region derived from the prokaryotic microorganism *E. coli*. Within the bacterial DNA region is a prokaryotic origin-replicator region. YEp13 has initial selectable markers for ampicillin and tetracycline resistance, and the LEU2 gene of the leucine biosynthetic pathway.

YEp13 plasmid was isolated from *E. coli* by the Birnboim-cesium chloride gradient method. Birnboim, H. C., Doly, J. (1979), *Nucleic Acid Research*, Vol. 7, 1513 ∝ 1523. About 50 micrograms (ug) YEp13 plasmid was digested with about 150 units of HindIII restrictase (Bethesda Research Laboratories, hereinafter BRL) in about 2 milliliters (ml) of 60 millimolar (mM) sodium chloride, 7 mM tris(hydroxymethyl)amino methane (TRIS), 7 mM magnesium chloride at pH 7.5 and 37° C. After 3 hours in these conditions, the digestion mixture was heated to 65° C. for 3 minutes followed by quenching on ice to inactivate the HindIII restrictase. Sodium chloride, beta-mercaptoethanol and initial BamHI restrictase (BRL) was added to the above mixture for a final amount of 100 mM, 10 mM, and 150 units, respectively. This mixture was incubated for 3 hours at 37° C., followed immediately by heating to 65° C. for 3 minutes and quenching on ice. The digested plasmid DNA was then concentrated by precipitation in 0.3 molar final concentration sodium acetate and 2.5 volumes of 95% ethanol. The concentrated DNA was resuspended twice in ethanol and the pellet was then redissolved in 80 microliters (ul) of 10 mM of TRIS-chloride at pH 8.0 containing 1 mM ethylenediamine tetracetic acid (EDTA).

The BamHI/HindIII digested YEp13 yielded a 10.3 kilobase fragment and a 0.4 kilobase fragment as determined by electroelution, using a buffer of 40 mM TRIS, 1 mM EDTA adjusted to pH 8.2 using glacial acetic acid, on a 0.8% agarouse horizontal gel, run at 30 volts for 15 hours. The 10.3 kilobase fragment thus obtained, was twice extracted in phenolchloroform (1:1 v/v) in the presence of 0.5 molar sodium chloride, followed by extraction twice with ether. The 10.3 kilobase fragment was precipitated in ethanol, then washed in ethanol and redissolved in 400 ul of TRIS EDTA buffer at pH 8.0. The redissolved pellet was reprecipitated and washed in ethanol and finally resuspended in 50 ul of 10 mM of TRIS-chloride buffer at pH 8.0.

The YEp13 vector thus obtained was a linear 10.3 kilobase plasmid having one "sticky" BamHI end and one "sticky" HindIII end, and was of suitable purity for cloning of a DNA fragment having therein a nucleotide sequence coding for the Mtx$^r$ DHFR gene therein.

Figure 3:
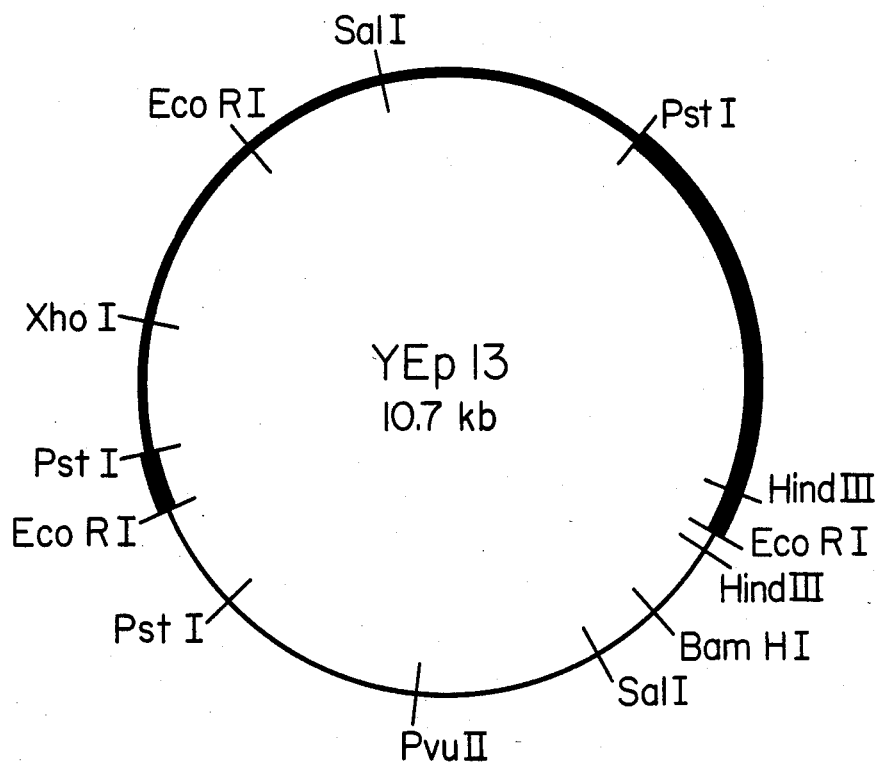
FIG. 3 is a schematic restriction map of YEp13.

With reference to FIG. 3, depicting a restriction map of YEp13, it should be noted that the region between the first HindIII site and the BamHI site, including the EcoRI site, clockwise from the first HindIII site and the second HindIII site clockwise from the above mentioned EcoRI site, is removed from the native YEp13 plasmid to form the linear 10.3 kilobase plasmid prepared by the method described above. As a result of this excision, the 10.3 kilobase fragment lacks a functional tetracycline resistance gene which is present in the region of the BamHI site in the native YEp13 plasmid. Furthermore, thorough digestion with the HindIII restrictase results in a vector having an insertion site which is contiguous with the yeast portion of the 10.3 kilobase fragment. The 10.3 kilobase fragment also contains a gene coding for amplicillin resistance, derived from *E. coli* and the LEU2 gene coding for an enzyme in the leucine biosynthetic pathway, derived from *S. cerevisiae*.

Isolation of the Nucleotide Sequence Coding of Mtx$^r$ From pFE364

*E. coli* carrying the plasmid pFE364, including a prokaryotic Mtx$^r$ DHFR nucleotide sequence, were obtained from M. Fling, Wellcome Research Labortories, North Carolina. Fling, M. E. and Elwell, L. P. (1980) *Journal of Bacteriology*, Vol. 141, 779-785. The plasmid was prepared by the Birnboim-cesium chloride gradient method except that *E. coli* cells containing pFE364 were grown in the presence of 10 ug per ml of trimethoprim (Sigma), a methotrexate derivative, instead of 100 ug per ml of ampicillin. The pFE364 plasmids, obtained by the following protocol, were pooled for the isolation of the nucleotide sequence coding for Mtx$^r$ DHFR.

One hundred micrograms (100 ug) of pFE364 plasmid was digested with 16 units BamHI (BRL) and 36 units ECoRI (Biolabs) restrictases at 37° C. for about 16 hours in 150 ul of 20 mM of TRIS-chloride, pH 7.0, 7 mM magnesium chloride, 100 mM sodium chloride, 2 mM beta-mercaptoethanol (Sigma). The 2.5 kilobase BamHI/EcoRI fragment containing the Mtx$^r$ DHFR gene was isolated from the remainder of the plasmid by electroelution on a 1.2% horizontal agarose gel run at 30 volts for 16 hours and an additional 150 volts for 3-4 hours. Buffer for the electroelution was as described above. The BamHI/EcoRI Mtx$^r$ DHFR fragment was collected and purified by extraction in phenol two times, extraction in chloroform one time and sequential precipitations in isopropyl alcohol and ethanol. The final DNA precipitate of approximately 10 ug, was resuspended in 100 ul 10 mM TRIS chloride, pH 8.0, 0.1 mM EDTA buffer. This same procedure was used for each batch. All three batches of the BamHI/EcoRI Mtx$^r$ DHFR fragment was pooled and precipitated in ethanol for digestion with HaeIII and AluI as described immediately below.

Approximately 30 ug of the BaMHI/EcoRI fragment was resuspended in 80 ul of a solution containing 50 mM TRIS chloride, pH 7.5, 5 mM magnesium chloride, 0.5 mM dithiothreitol to which was added 5 ul containing 45 units of stock HaeIII restrictase (BRL). The mixture was incubated at 37° C. for 2 hours, at which time 10 ul of 50 mM sodium chloride and 5 ul containing 40 units of stock AluI restrictase (BRL) were added. This digestion mixture was further incubated for 2 hours at 37° C.

A 370 base pair HaeIII/AluI DNA fragment having a nucleotide sequence coding for Mtx$^4$ DHFR therein was isolated by electroelution on a 2% agarose horizontal gel at 150 volts, for 2 hours. The elution buffer was as described above. The HaeIII/AluI fragment was purified by extraction in phenol 3 times, extraction in chloroform 2 times, and precipitation twice in 0.3 molar sodium acetate-ethanol. The working solution contained about 7.5 ug of DNA fragment having a nucleotide sequence coding for Mtx$^r$ DHFR therein and a total volume of 50 ul of 10 mM TRIS-chloride buffer, pH 8.0, 0.1 mM EDTA.

Ligation of Mtx$^r$ DHFR Nucleotide Sequence Linkers

Prior to ligation with the 370 base pair DNA fragment having a nucleotide sequence coding for MTX$^r$ DHFR therein, terminal phosphate groups were restored to the linker molecules. Five micrograms of the proper octanucleotide linker (Collaborative Research) was suspended in a total volume of 10 ul containing 70 mM TRIS-chloride, pH 7.5, 10 mM magnesium chloride, 5 mM dithiothreitol (Sigma) and 50 ul 32 phosphate (32P) adenosine triphosphate (ATP). The mixture was heated to 70° C. for 2 minutes before addition of 5.5 units of T4 polynucleotide kinase (BRL). After 30 minutes at 37° C., the mixture was supplemented with 5.5 units kinase enzyme 1 mM non-labeled ATP and incubated an additional 30 minutes. The reaction was then inactivated at 65° C. for 10 minutes and stored at −20° C. Phosphorylated linkers were self-ligated to test for effective phosphorylation. Phosphorylation of the linkers was indicated by extensive ladder formation of the self-ligated linkers on a 7% acrylamide gel as visualized by conventional autoradiographic techniques. Redigestion of self-ligated linkers with HindIII and BamHI in appropriate conditions regenerated linker monomers.

Prior to ligation with the restored linkers, the DNA fragment having a nucleotide sequence coding for Mtx$^r$ DHFR therein having unpaired terminal bases was treated with DNA polymerase I in the presence of deoxynucleotides so that unpaired bases were complemented. Approximately 1 ug of the purified DNA fragment having a nucleotide sequence coding for Mtx$^r$ DHFR therein was incubated with 2 units of DNA polymerase I (BRL), 10 mM beta-mercaptoethanol, 60 mM TRIS-chloride, pH 7.5, 8 mM magnesium chloride and 0.2 mM of deoxyadenosine triphosphate, deoxycytidine triphosphate, deoxythymidine triphosphate, and deoxyquanosine triphosphate (P. L. Biochemicals) in 20 ul total volume at 16° C. for 60 minutes. The reaction was then inactivated by heating at 65° C. for 10 minutes and quenching on ice. The DNA fragment having a nucleotide sequence coding for Mtx$^r$ DHFR therein was now ready for blunt-end ligation to the BamHI and HindIII octanucleotide linkers.

Blunt-end Ligation of DNA Fragment Having a Nucleotide Sequence Coding For Mtx$^r$ DHFR Therein to Octanucleotide Linker Beta-mercaptoethanol was added to the above Mtx$^r$ DHFR mixture to a final concentration of 10 mM. About 1 ug of each $^{32}$p-phosphorylated BamHI and HindIII linkers were also added. Blunt-end ligation was performed in 40 ul containing the Mtx$^r$ DHFR fragment (1 ug), linkers, 200 units of T4 DNA ligase, 66 mM TRIS chloride, pH. 7.5, 6.6 mM magnesium chloride 0.25 mM ATP and 10 mM dithiothreitol at 20° C. for 20 hours. The ATP mixture was heat-inactivated and then supplemented with 60 mM final concentration sodium chloride. The ligation mixture was digested with 6 units HindIII restriction enzyme for 2.5 hours at 37° C. Eight units BamHI restrictase, 2 mM beta-mercaptoethanol and sufficient sodium chloride to give 100 mM final concentration was added directly to the above mixture. Digestion was conducted at 37° C. for 2.5 hours. The DNA fragment having a nucleotide sequence coding for Mtx$^r$ DHFR therein ligated to the BamHI and HindIII linkers was concentrated by precipitation in ethanol followed by purification from free linkers by electroelution on a 2% agarose horizontal gel at 150 volts for about 1.5 hours using the buffer described previously. The electroeluted fragment was extracted with phenol followed by extraction with ether and then precipitated and washed in ethanol. The DNA fragment having a nucleotide sequence coding for Mtx$^r$ DHFR therein now contained one or more terminal BamHI and/or HindIII octanucleotide linkers for cloning into the BamHI/HindIII digested YEp13 vector.

Ligation of the DNA fragment having a nucleotide sequence coding for Mtx$^r$ DHFR therein to the YEp13 vector was carried out in a total volume of 30 ul by adding together 1.8 ug of purified BamHI and HindIII digested YEp13 in the form of a linear 10.3 kb fragment, 0.06 ug of purified DNA fragment having a nucleotide sequence coding for Mtx$^r$ DHFR therein ligated to $^{32}$P-phosphorylated BamHI and/or HindIII linkers, 21 ug per ml of bovine serum albumin (BRL), 1 mM ATP (Sigma), 30 mM TRIS-chloride, pH 7.5, 10 mM magnesium chloride, 50 mM sodium chloride, and 10 mM betamercaptoethanol. The mixture was heated at 37° C. for 2 minutes, then 200 units of T4 DNA ligase was added. The ligation was conducted for 24 hours at 4° C. The resulting mixture contained a variety of free DNA species as well as partial and complete ligation products.

Transformation of E. coli with Mtx$^r$ DHFR Ligation Products

E. Coli strain LE 392 was cultured in 15 ml of Luria-broth (L-broth) at 37° C., in a rotating incubator at 200 rpm to an optical density of 0.6 at 600 nanometers. The cell solution was chilled for 5 minutes on ice, centrifuged in a tabletop centrifuge at approximately 5000 rpm and the pellet was resuspended in 10 ml of 10 mM magnesium sulfate. The cells were washed with magnesium sulfate, centrifuged, and resuspended in 2.5 ml of chilled 50 mM calcium chloride. The cells were maintained in a calcium chloride solution on ice for about 30 minutes, after which they were again centrifuged and resuspended in 1 ml of 50 mM calcium chloride. One hundred microliters of the suspended *E. coli* cells was added to 30 ul of the previously obtained ligation mixture in a sterile 1.5 ml Eppendorf tube. Transformation was conducted at 0° C. for 45 minutes. The cells were then resuspended in 2 ml of L-broth and allowed to incubate at 37° C. for approximately 1 hour, after which the culture was centrifuged and the cell pellet resuspended in 1 ml of 10 mM magnesium sulfate. Approximately 100 ul of this solution was then incubated on Luria-agar (L-agar) medium plates containing 100 ug per ml ampicillin (Sigma). Plates were incubated for 16 hours at 37° C. Seventeen amplicillin-resistant colonies were obtained.

Analysis of E. coli Transformants for the $Mtx^r$ DHFR Containing Nucleotide Sequence Four *E. coli* transformants obtained by the above-described methods and designated 2, 3, 4, and 5, were analyzed for the presence of the $Mtx^r$ DHFR-containing DNA fragment insert by a number of methods, including estimation of plasmid size by agarouse gel electrophoresis, estimation of the BamHI/HindIII restriction enzyme digest using acrylamide gel electrophoresis and hybridization of the original DNA fragment containing an nucleotide sequence coding for $Mtx^r$ DHFR therein labelled with $^{32}P$ to Southern blots of total cellular DNA from a transformat. Plasmids designated respectively MTX2 MTX3, MTX4 and MTX5 were isolated from the abovementioned transformants by the following procedure. Cells of each transformant were separately incubated at 37° C. with agitation at 250 rpm in 50 ml of L-broth containing 100 ug per ml of ampicillin until the cells reached an optical density of between 1.1 to 1.3. Fifteen milligrams of spectinomycin (UpJohn) was then added. After an additional period of growth for 15 hours under the same conditions, the cells were harvested by centrifugation in a Sorvall SS-34 rotor, in sterile polypropylene screwcap tubes. The cell pellet was resuspended in 2 ml of a solution containing 5 mM glucose, 10 mM EDTA, 25 mM TRIS-chloride buffer, pH 8.0, and 2 mg per ml of egg white lysosyme, Grade I (Sigma). After holding the cells at 0° C. for 30 minutes, they were thoroughly mixed with 4 ml of a solution containing 0.2 normal sodium hydroxide and 1% sodium dodecyl sulfate, to obtain a clear lysate. After 5 minutes at 0° C., the lysate was treated with 3 ml of 3 molar sodium acetate, pH 4.8, mixed thoroughly and incubated at 0° C. for one hour. Cellular debris were precipitated by centrifugation. Eight ml of the supernatant containing plasmid DNA was transferred to a fresh tube and the DNA was precipitated in 20 ml of ice cold ethanol at −35° C. for 20 minutes. The plasmid DNA was collected by centrifugation and resuspended in 2 ml of a solution containing 50 mM TRIS-chloride, pH 8, 0.2 M lithium chloride, 20 mM EDTA and 0.2% sodium dodecyl sulfate. The DNA was extracted with an equal volume of chloroform-phenol at about 1:1 v/v. The plasmid containing phase was separated from phenol by centrifugation. Approximately 1.6 ml of the DNA solution was transferred to a fresh tube and precipitated in ethanol, resuspended in 0.5 ml of 0.3 molar sodium acetate in distilled water and reprecipitated in ethanol. The DNA pellet thus obtained was dissolved in 0.2 ml of 10 molar TRIS-choride, pH 8.0, for treatment with 20 ug per ml of RNase at 37° C. for 30 minutes. Following the third ethanol percipitation, the plasmid DNA was resuspended in 50 ul of distilled water. One microliter of each of the plasmids, prepared by the above-described methods was run on a 0.7% agarose horizontal gel at 25 volts for 18 hours along with standard plasmids of known size. Each of the MTX plasmids was about 10.7 kilobases in size.

Each of the MTX plasmids was further characterized by electroelution of 5 ul of the plasmid suspension containing approximately 0.3 ug of the plasmid on an agarose gel in order to obtain plasmids free of contaminating ribonucleic acid. Each plasmid was then digested using methods essentially similar to those described hereinabove, with BamHI, 4 units, and HindIII, 8 units, for fragment size analysis on a 4% acrylamide gel run at 150 volts for 3 hours in 89 mM TRIS-chloride, pH 8.3, 2.5 mM EDTA, 89 mM borate buffer. Each of the smallr plasmid fragments from the MTX plasmids was approximately 0.37 to 0.38 kilobases when compared to standards of known size. The larger fragment of each MTX plasmid was approximately 10.5 to 10.7 kilobases as determined on a 1% agarose gel run at 50 volts for 9 hours in 3 ml TRIS-chloride, pH 8.2, 1 mM EDTA, 5 mM sodium acetate. These fragments were consistent with the sizes expected for the DNA fragment having a nucleotide sequence coding for $Mtx^r$ DHFR therein cloned into BamHI/HindIII digested-YEp13.

Characterization by Hybridization Studies

DNA from each of the 17 *E. coli* transformants was hybridized to the 370 base pair DNA fragment having a nucleotide sequence coding for $Mtx^r$ DHFR therein labelled with $^{32}P$ by nick translation using a technique called "colony-hybridization". Both of these techniques are commonly known to those skilled in the art. (Southern, E. (1975), *Molec. Biol.*, Vol. 98, 503–517; Gruenstein, M. and Hogness, D. S. (1975), *Proc. Natl. Acad. Sci.*, Vol. 72, pp 3961–3965; Rigby, P. W., Drickmann, M. Rodes, C. and Bug, P. J. (1977), *Mol. Biol.*, Vol. 113, p 237. Hybridization was detected by autoradiography on Kodak X-OMAT AR-5 film. Fourteen transformants, including 2, 3, 4, and 5, contained DNA homologous to the original $MTX^r$ DHFR insert.

Expression of the Cloned $Mtx^r$ DHFR in *E. coli*

Five *E. coli* transformants, including MTX3 and MTX5 and three others which lacked the $Mtx^r$ DHFR insert grew poorly on L-agar medium containing 25 ug per ml trimethoprim (Sigma) after 15 days at room temperature. Growth of these transformants was sparse and uneven in density. *E. coli* LE392 having no MTX-containing plasmid was similar in appearance.

Twelve *E. coli* transformants, including MTX2 and MTX4, gave heavy and confluent growth under the same conditions on L-agar with trimethoprim, suggesting that the $Mtx^r$ DHFR was expressed partially or fully in MTX2 and MTX4.

Orientation of the $Mtx^r$ DHFR Nucleotide Sequence Within the Vector

Figure 2:
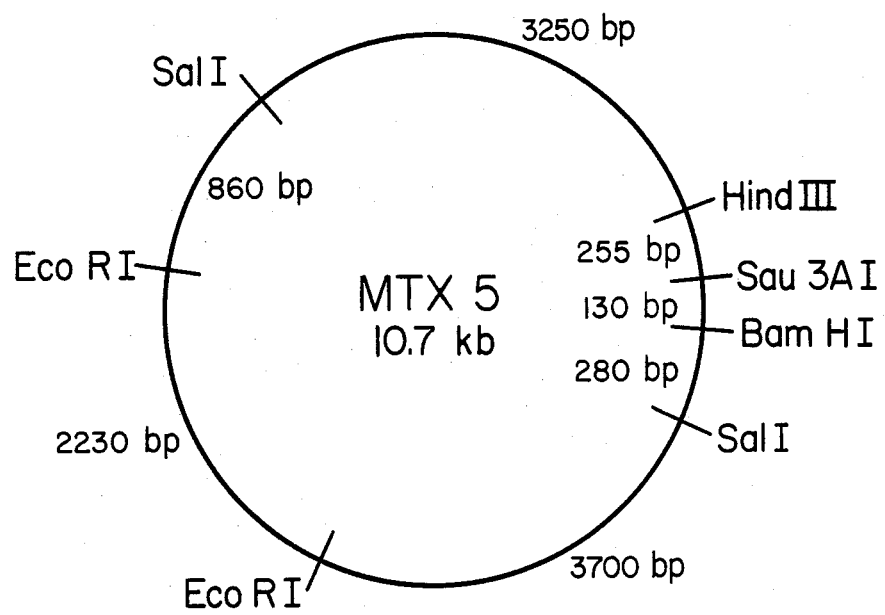
FIG. 2 is a schematic restriction map of MTX5, a variant of MTX4 also having therein a nucleotide sequence coding for Mtx$^r$ DHFR therein.

Further analysis of plasmid MTX2, MTX3, MTX4, and MTX5 using digestion by SAU 3A I and BamHI indicate that the $Mtx^r$ DHFR insert is oriented such that transcription of the $Mtx^r$ DHFR insert in the MTX2 and the MTX4 plasmid proceeds from the HindIII region to the BamHI region of the plasmid, whereas transcription of the $Mtx^r$ DHFR insert in the MTX3 and MTX5 proceeds from the BamHI site to the HindIII site in the opposite direction with the vector. This orientation is more clearly illustrated in FIGS. 1 and 2. As can be seen from FIGS. 1 and 2, the nucleotide sequence coding for $Mtx^r$ DHFR has a Sau 3A I restriction site which is located acentrically within the nucleotide sequence. Analysis of the size of digestion fragments using BamHI and Sau 3A I was used to determine the orientation of the Mtx$^r$ DHFR nucleotide sequences in the plasmid.

The method for carrying out the digestion and analysis of the plasmid fragments is well known to those skilled in the art and is briefly summarized as follows. Each of the plasmids was digested with BamHI. Terminal phosphates were removed by alkaline phosphatase digestion, followed by phenol extraction to remove alkaline phosphatase. After removal of the residual phenol by repeated ether extraction, the digested plasmid DNA was precipitated by ethanol-acetate and redissolved in distilled water. Radiolabelling of terminal phosphates of the respective plasmids was carried out in an approximate kinase buffer using T4 polynucleotide kinase (BRL) and $^{32}$P-labelled ATP followed by an additional pulse of non-labelled ATP. After radiolabelling, the mixture was extracted in phenol, then ether, and precipitated in sodium acetate-ethanol as above. The respective plasmids with $^{32}$P-labelled terminal phosphate groups were then digested with Sau 3A I restrictase (Biolabs) in an appropriate buffer for a period sufficiently long for essentially complete digestion. The digested plasmid DNA fragments were concentrated by ethanol precipitation and run in an appropriate buffer on 6% acrylamide gel for a sufficient period of time to completely separate the migrating DNA fragments. The BamHI/Sau 3A I fragments were visualized by autoradiography on Kodak X-OMAT AR-5 film for 4.5 days. Reference DNA fragments of standard sizes were run to calculate the sizes of the BamHI/Sau 3A I DNA fragments.

Transformation of Yeast by MTX2, MTX3, MTX4 and MTX5

S. cerevisiae strain DBY-746 was transformed with 5 to 10 ug of plasmids MTX2, MTX3, MTX4, and MTX5 carrying the Mtx$^r$ DHFR gene. (S. cerevisiae strain DBY-746 was obtained from R. K. Mortimer, University of California, Berkeley, Calif.) Yeast cells, grown in 50 ml of yeast extractant peptone dextrose broth to a final optical density of 0.6 to 0.7 at 600 nanometers were washed once in 10 ml sterile 1 molar sorbitol solution and collected by centrifugation. The cell pellet was resuspended in 4 ml sorbitol plus 10 ul beta-mercaptoethanol (Sigma) for 15 minutes at 30° C. Following another sorbitol wash, cell walls were removed by treatment with 0.5 mg Zymolyase 60,000 enzyme (Kirin) at 30° C. for 60 minutes. Spheroplast yeast cells appearing spherical due to loss of the cell wall, were obtained in highest yields in 50 ml capped polypropylene tubes incubated without agitation. The spheroplasts were washed in 10 ml sorbitol and harvested by centrifugation at 1500 rpm, for 12 minutes at 4° C. Residual Zymolyase was removed by an additional wash with 20 ml of sorbitol. The spheroplasts were then incubated in 67% YEPD broth containing 1 molar (M) sorbitol for 45 minutes followed by washing with sorbitol and resuspension in 0.8 ml of 1M sorbitol, 10 mM TRIS buffer, pH 7.5, 10 mM calcium chloride for transformation.

The yeast transformation mixture included approximately 3 to 5 ug of the respective plasmid DNA, 0.1 ml of yeast spheroplasts and 1 ml of freshly made sterile 40% polyethylene glycol 4000 (aqueous) in 10 mM TRIS, pH 7.5, 10 mM calcium chloride. Following preincubation of the plasmid DNA and the spheroplasts at room temperature for 15 minutes, transformation was carried out on ice for at least one hour in 1.5 ml Eppendorf tubes. About 0.1 ml of the transformation mixture was diluted in 10 ml regeneration medium containing one molar sorbitol, 0.67% yeast nitrogen base without main amino acids (Difco), 2% glucose (Baker), 3% agar (Difco), 20 mg per liter adenine sulfate, uracil, histidine, arginine, tryptophan, and methionine, 30 mg per liter tyrosine, isoleucine, and lysine, 50 mg per liter phenylalanine, 100 mg per liter glutamic acid and aspartic acid, 150 mg per liter valine, 200 mg per liter threonine and 375 mg per liter serine. All nucleotide an amino acid supplements were purchased from Sigma Chemicals. The regeneration suspension was mixed and poured over agar which contained all the above constitutents except for sorbitol. Transformants were visible after four days at 30° C. Yeast transformants were selected from the regeneration plates and maintained on minimal medium without leucine. Yeast transformants, selected by ability to grow in the absence of leucine, confirmed the presence of the LEU2 gene of plasmid. The yeast transformants so obtained were further tested for resistance to methotrexate.

To test for methotrexate resistance, a minimal medium appropriate for growth of S. cerevisiae but that lacked leucine and contained methotrexate at 1 mM was prepared. Three different yeast transformants containing either YEp13, MTX4 or MTX5 plasmids were grown on this medium for a sufficient period of time to assure growth. The growth of YEp13 and MTX4-containing yeast transformants was visibly inhibited but the growth of the MTX5-containing yeast transformant did not display the same inhibition.

EXAMPLE II

Preparation of Hybrid Plasmids Carrying the Mtx$^r$ DHFR Nucleotide Sequence and 480-Base pair Fragment Having a Plant Promoter Region Therein Preparation of MTX4 Vector DNA MTX4 plasmids were prepared by the Birnboim-cesium-chloride gradient method as above. Approximately 15 ug MTX4 was digested with 5 units of HindIII restrictase (Biolabs) in 50 ul of 7 mM TRIS-chloride, pH 7.5, 7 mM magnesium chloride, 60 mM sodium chloride for 3.5 hours at 37° C. To this reaction mixture was added 1 microliter of 2M TRIS-chloride buffer, pH 8.0, to give a final concentration of 40 mM, and 1 ul containing 3.3 units of calf alkaline phosphatase (Boehringer Mannheim). This mixture was incubated at 65° C. for 20 minutes followed by extraction once in phenol which was previously equilibrated with TRIS-sodium chloride-EDTA at pH 7.0, and twice in chloroform. The DNA was precipitated twice in 95% ice cold ethanol plus 0.3 molar sodium acetate at −35° C. for 45 to 60 minutes. The DNA was resuspended in distilled water.

One microliter of the MTX4 preparation obtained as above was checked for ligation using 200 units T4 DNA ligase (Biolabs) in a total volume of 20 ul of appropriate buffer salts for 2 hours at room temperature. Virtually, all the phosphatase-treated MTX4 remained in the linear form, as analyzed by agarose gel electrophoresis with suitable standards. However, the untreated MTX4 preparation gave almost total conversion to more slowly migrating species indicating efficient ligation.

The final MTX4 vector was resuspended in 11 ul of distilled water. At this point, the 10.7 kilobase vector was a linear molecule cut with HindIII, having unpaired bases at each end and the terminal phosphate groups removed to prevent self-ligation.

Preparation of the 480 base pair Fragment with HindIII Linkers

The 480-base pair fragment is originally a portion of *Agrobacterium tumefaciens* tumor-inducing plasmid A6 (pTiA6). To obtain the 480-base pair fragment, pTiA6 is digested with HindIII restrictase. A 2.75 kg fragment having HindIII ends is isolated by agarose gel electrophoresis. The 2.75 kb fragment is electroeluted, concentrated by ethanol precipitation, and resuspended in distilled water. An aliquot of the 2.75 kb fragment DNA is supplemented with salts required for Sau 3A1 restrictase digestion and Sau 3A1 restrictase, and is allowed to digest for a period of time sufficient to assure essentially complete digestion. A digestion mix of the 2.75 kg fragment contains a number of fragments, only two of which have one Sau 3A1 end and one HindIII end. One of these two fragments is the 480-base pair fragment.

pR4269 is obtained by digesting pBR327 with Bam HI and HindIII. Upon purification, a linear DNA fragment having one Bam HI "sticky" end and one HindIII "sticky" end is obtained. This fragment is incubated with the previously obtained Sau 3A 1 digestion mix of the 2.75 kb fragment along with T4 ligase and ATP in an appropriate buffer for ligation. Because BAM HI "sticky" ends are compatible with Sau 3A 1 ends, the two fragments having one Sau 3A 1 end and one HindIII will ligate to the Bam HI/HindIII digested pBR327 to yield covalently closed circular (ccc) DNA plasmids. Of the two ccc plasmids, the one having a 480-base pair fragment ligated therein is designated pR4269.

Sequence analysis of the 480-base pair fragment using techniques well known to those skilled in the art (see BRL User Manula, M13 Cloning/Dideoxy" sequencing Manual ©1980 BRL Inc., Gaithersburg, Md. 20760) yielded the following sequence:

```
         10         20         30
    AAGCTTGAAAATTAAGCCCCCCCCCGAAAT
    HindIII 40         50         60
    CATCGCCACAGGTCGTCCCAGCCCGGCATC 70         80         90
    TATATATAGCGCCAATATAGTTTGTCTTAC 100        110        120
    ACAAACACACCTCACATCATGAATTTCGCA 130        140        150
    GATACTCCTTGGCCTCCCTCGACCTAGACT 160        170        180
    GGGCATGCGAAGAGTTTATCAAAACTTATG 190        200        210
    GTGCATCTCCACAATTGGAAACAGGAGAGG 220        230        240
    TAATCCAAACAAACAATGGGCTGCTGTATT 250        260        270
    TGTATGGCAAAGGTTCACTCTCACAGCGGA 280        290        300
    TTCATGACAJACACCTCAAATTTAAGGAGA 310        320        330
    AGGAAGGATTATCCTTCACTACCATAAAGC 340        350        360
    CAGCTGAGATGAAGGCGCAACAAAGTGATT 370        380        390
    TAACTTATTATGTCGCCATTTTTCAAAGCA
```

```
                -continued
        400        410        420
    ACTATTTCCTGTGCGTTTCAAATCCAGAGA 430        440        450
    AAGGCTTTCTGAGA9TGCCATAATCGCCCA 460        470        480
    TTTCTGTACCCCATAGTAGCCCATGGATCC
                                BamHI
``` wherein J is C or G and A is adenine, T is thymine, C is cytosine and G is guanine number 9 indicates an ambiguous base assignment which may be adenine at site 435.

The 480 base pair fragment was excised from *E. coli* plasmid pR4269. One hundred microliters of pR4269, obtained by the Birnboim cesium chloride method as above, containing 25 ug of plasmid DNA was digested with 10 units HindIII restrictase for about 11 hours at 37° C. in 150 ul HindIII buffer salts. After supplementation with sodium chloride and TRIS-chloride at pH 7.0, to final concentrations of 100 mM and 20 mM, respectively, 8 units of BamHI restrictase was added to the digest. After reacting for 9 hours at 37° C., an additional 5 units of HindIII and 4 units of BamHI were added. After 12 hours at 37° C., the digest was further supplemented with 5 units HindIII and 4 units BamHI and digested at 37° C. for three hours. The 480 base pair fragment was electroeluted in appropriate buffer on a 0.7% agarose gel at 125 volts for 2 hours. The 480 base pair fragment was purified by 3 extractions in phenol, 3 extractions in chloroform, and 2 precipitations in ethanol under conditions similar to those used in Example I above. The purified 480-base pair fragment thus obtained was resuspended in 50 ul of distilled water at a concentration of approximately 0.2 ug per ml.

The 480-base pair fragment contained one HindIII cut end and one BamHI cut end. To complement terminal unpaired bases of the 480-base pair fragment, about 3 ug of the 480-base pair fragment was incubated with about 10 units of Klenow fragment enzyme (BRL, large sub-unit of *E. coli* DNA polymerase I) in the presence of 0.2 mM each of deoxyadenosine-5'-triphosphate, deoxycytidine-5'-triphosphate, deoxythymidine-5'-triphosphate and deoxyguanosine-5'-triphosphate (P.L. Biochemicals) in 20 mM betamercaptoethanol, 60 mM TRIS-chloride, pH 7.5, and 8 mM magneisum chloride at a total reaction volume of approximately 22 ul. After 60 minutes at 16° C. the mixture was heat inactivated to 65° C. for 10 to 12 minutes.

Prior to ligating the 480-base pair fragment to HindIII linkers, terminal phosphate groups were restored to the linker molecules by the same procedure used in Example I above except that instead of $^{32}$P-labeled ATP, the ATP was unlabeled. To ligate the 480-base pair fragment, 22 ul of the polymerase mixture containing about 3 ug of 480-base pair fragment was added to 10 ul of the HindIII linker mixture at a molar ratio of linker to fragment of about 100:1. To this solution was added 4 ul of ligase buffer salts containing 66 mM TRIS-chloride, pH 7.5, 66 mM magnesium chloride, 10 mM dithiothreitol, 0.6 ul of 10 mM ATP, 1 ul of 0.2 mM beta-mercaptoethanol and 100 units of T4 DNA ligase in 40 ul total volume. The mixture was incubated at between 20° to 22° C. for 9 hours and was further supplemented with 100 units of ligase and then incubated for an additional 40 hours.

480-base pair fragments with HindIII "sticky" ends were generated by treating the ligation mixture obtained immediately above with 10 units of HindIII restrictase enzyme at 37° C. for 4 hours after addition of sodium chloride directly to the ligation solution and adjustment of the volume to 50 ul with distilled water. The 480-base pair fragment having HindIII "sticky" ends was separated from free linkers by precipitation with ethanol in the presence of 100 mM sodium chloride and 10 mM spermine (Sigma) at 0° C. for 15 minutes. The pellet was collected by cold centrifugation for 10 minutes and resuspended in 5 ul of 200 mM TRIS-chloride, pH 7.5, 7 mM magnesium chloride, 1 molar sodium chloride and 2 mM beta-mercaptoethanol. This solution was diluted with 45 ul of distilled water and twice reprecipitated in 5 mM spermine. The 480-base pair fragment was resuspended in 8 ul of ligase buffer containing 150 mM TRIS-chloride, pH 8.0, 50 mM magnesium chloride, 250 mM sodium chloride, 50 mM beta-mercaptoethanol, and 250 ug per ml of bovine serum albumin (BRL).

Upon treatment of the thus obtained 480-base pair fragments having HindIII linkers on the ends thereof with ligase in 1 mM ATP, the fragment formed multimers which were converted to monomeric species after HindIII digestion. BamHI restrictase also converted multimers to monomers, which suggests that the terminal BamHI site of the fragment was reconstituted upon ligation to the HindIII linkers.

Ligation of the 480-base Pair Fragment to the MTX4 Vector

About 5 ug MTX4 plasmid, previously digested with HindIII restriction enzyme and phosphatase in a procedure essentially the same as that used for the 480-base pair fragment was added to 0.4 ug of the 480-base pair fragment having HindIII linkers on the ends thereof. Ligation was conducted in 30 mM TRIS-chloride, pH 8, 10 mM magnesium chloride, 10 mM beta-mercaptoethanol, 50 ug per ml bovine serium albumin, 1 mM ATP and 200 units of T4 DNA ligase in a total volume of 40 ul. After 2 hours at 20° C., the mixture was inactivated by heating at 65° C. for 10 minutes. Thirty microliters of the ligation mixture was used directly to transform *E. coli* cells.

Transformation of *E. coli* Cells

*E. coli* cells of strain LE392 were transformed using the thus obtained plasmid in a procedure essentially similar to that described in Example b 1, above for transformation of *E. coli* with Mtx$^r$ DHFR ligation products, except that the mixture used for transformation included MTX4 having the 480-base pair fragment ligated therein.

Clone Analysis 200 ampicillin-resistant colonies resulting from the transformation were screened for the 480-base pair fragments by the colony hybridization method described in Example I hereinabove under "Characterization by Hybridization Studies" except that a $^{32}$P-labelled 480-base pair fragment, generated by nick translation, was used.

Eleven colonies containing DNA that hybridized to the $^{32}$P-labelled 480-base pair fragment were analyzed for insert copy number and orientation. Plasmid DNA was isolated from 1.5 ml of cells grown in L-broth plus 100 ug/ml ampicillin (Sigma) by a modified method of Birnboim et al. In the modification, plasmid DNA from clarified supernatants was precipitated in ethanol, resuspended in 100 microliters of 10 mM TRIS pH 8, then treated with 100 ug/ml ribonuclease (Sigma) at 37° C. for 30 minutes instead of purified on cesium chloride gradients. Twenty-five ul of the plasmid solution was applied directly to a 0.8% agarose gel to estimate plasmid size. Nine clones contained plasmids larger than 10.7 kb. Each of the plasmids from the nine clones was ethanol-precipitated, then resuspended in 10 microliters of deionized water for digestion with Bam HI restriction enzyme. Following Bam HI digestion at 37° C. for 3 hours, one-half volume of each of the plasmid samples was reprecipitated in ethanol, dissolved in 44 ul of deionized water and then treated with 3 to 6 units PstI restrictase (Biolabs), in the appropriate buffer salts at 37° C. for 3 hours. Ethanol precipitates of the Bam HI and PstI digests of each plasmid sample were run in 1.0% agarose at 75 V for 5 hours. Digest of the cloning vector YEp13 generated fragments of known length and number that provided molecular size standards and confirmation of the completeness of the digestion. Lambda DNA predigested with Hind III and pBR327 plasmid DNA predigested with HinfI served as fragment size standards.

Orientation of the insert(s) could be determined by mapping of a uniquely reconstituted Bam HI site which occurred at a specific end of the 480-base pair fragment in the following way. The Bam "sticky" end of the 480-base pair fragment has the sequence 5' GATCC 3'-etc. This "sticky" end becomes a functional Bam restriction site, which has the sequence 5' GGATCC 3'-etc, when linked to Hind III linkers having the sequence 5' CAAGCTTG 3'-etc, to give 5' CAAGCTTGGATCC 3' etc. The 3'-terminal guanosine residue of the Hind III linker acts as the 5' initial guanosine residue of the Bam HI sticky end, thereby reconstituting the Bam HI restriction site. A tandem HindIII/Bam HI site results. Localization of this tandem HindIII/Bam HI site with respect to a second PstI restriction restriction site on the vector was used to determine orientation of the insert.

Analysis of MTX4/4269 Plasmids

Figure 4:
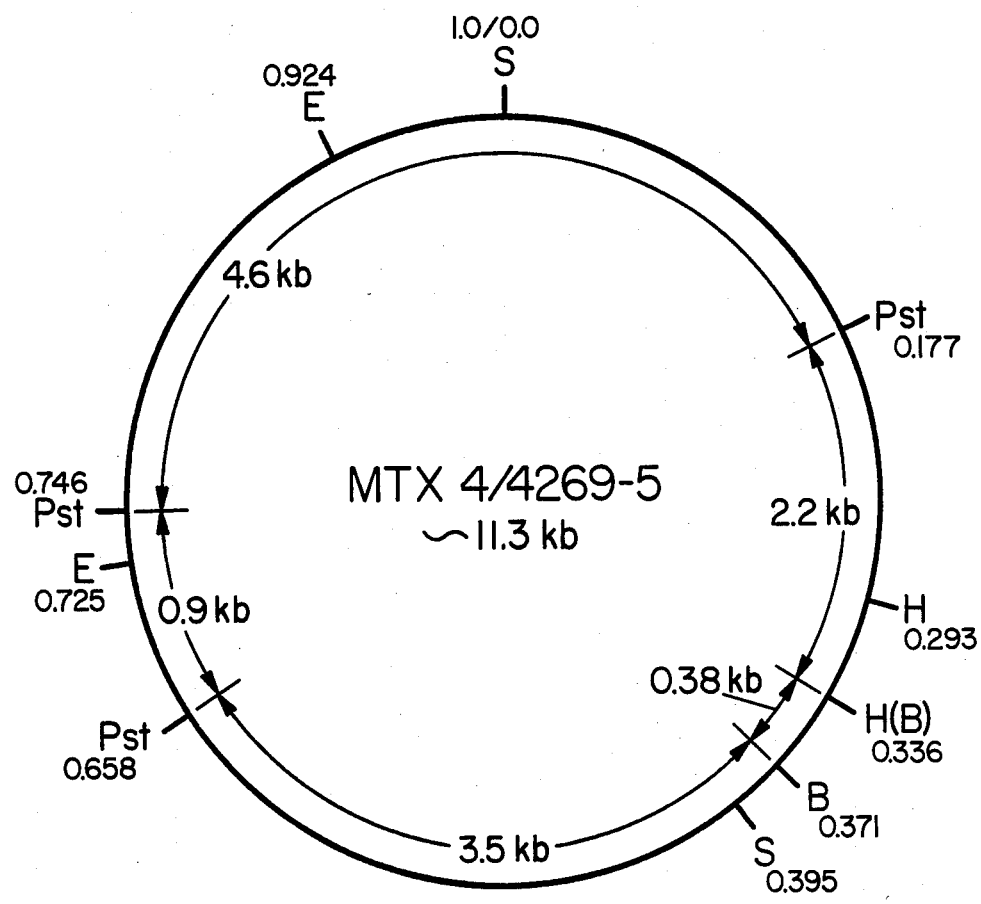
FIG. 4 is a schematic restriction map of MTX4/4269-5.

A plasmid designated MTX4/4269-5 obtained from the ligation of the 480-base pair fragment into MTX4 plasmid was digested with PstI and Bam HI restrictase and the fragments were resolved on a 1.0% agarose gel as described above. Five fragments having the following approximate size were resolved: 4.6 kb, 3.5 kg, 0.9 kb, 2.2 kb and 0.38 kb. FIG. 4 is a restriction map consistant with the fragment size obtained from MTX4/4269-5. The 2.2 kb fragment is comprised of the 480-base pair fragment and vector DNA. The 2.2 kb fragment was generated by Bam HI digestion of the above mentioned reconstituted Bam HI site and PstI digestion of one of the vector DNA PstI sites. The reconstituted Bam HI site is adjacent to the 0.38 kb fragment having the Mtx$^r$ DHFR nucleotide sequence therein.

Figure 5:
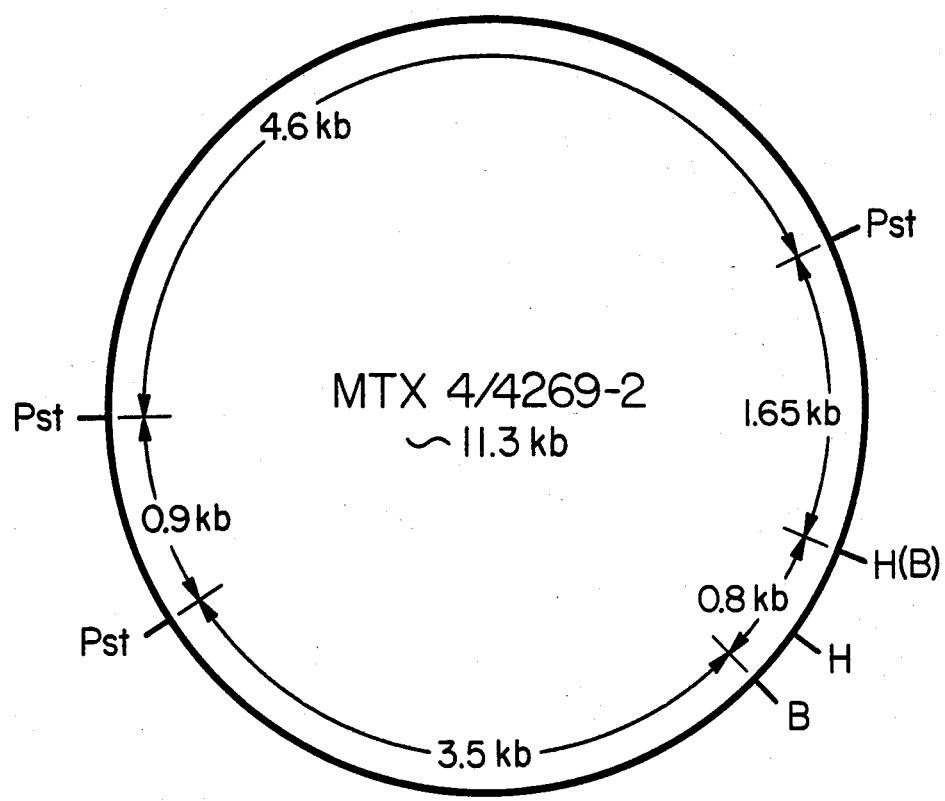
FIG. 5 is a schematic restriction map of MTX4/4269-2.

A plasmid MTX4/4269-2 was treated in the same manner as MTX4/4269-5. Five fragments having the following sizes were resolved: 4.6 kb, 3.5 kb, 1.65 kb, 0.9 kb and 0.8 kb. FIG. 5 is a restriction map consistent with these results. The 1.65 kb fragment was generated by PstI digestion of one of the vector DNA PstI sites and by Bam HI digestion of the adjacent reconstituted Bam HI site. The 0.8 kb fragment is comprised of the 480-base pair fragment and the DNA fragment having the nucleotide sequence coding for Mtx$^r$ DHFR therein.

Figure 6:
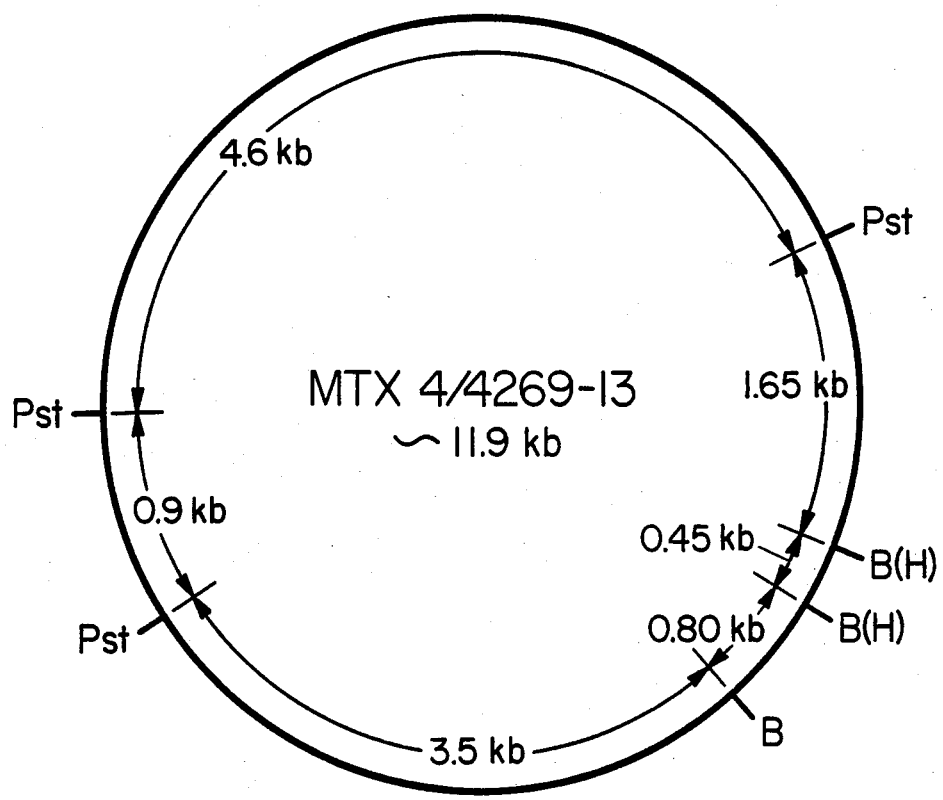
FIG. 6 is a schematic restriction map of MTX4/4269-13.

Another plasmid MTX4/4269-13 was digested in the same manner as MTX4/4269-2 and yielded 6 fragments of 4.6 kb, 3.5 kb, 1.65 kb, 0.9 kb, 0.8 kb and 0.45 kb. FIG. 6 is a restriction map consistent with these results. The 0.45 kb fragment indicates the presence of at least two 480-base pair fragments tandemly inserted in the same orientation as the single 480-base pair fragment of MTX/4629-2.

Figure 7:
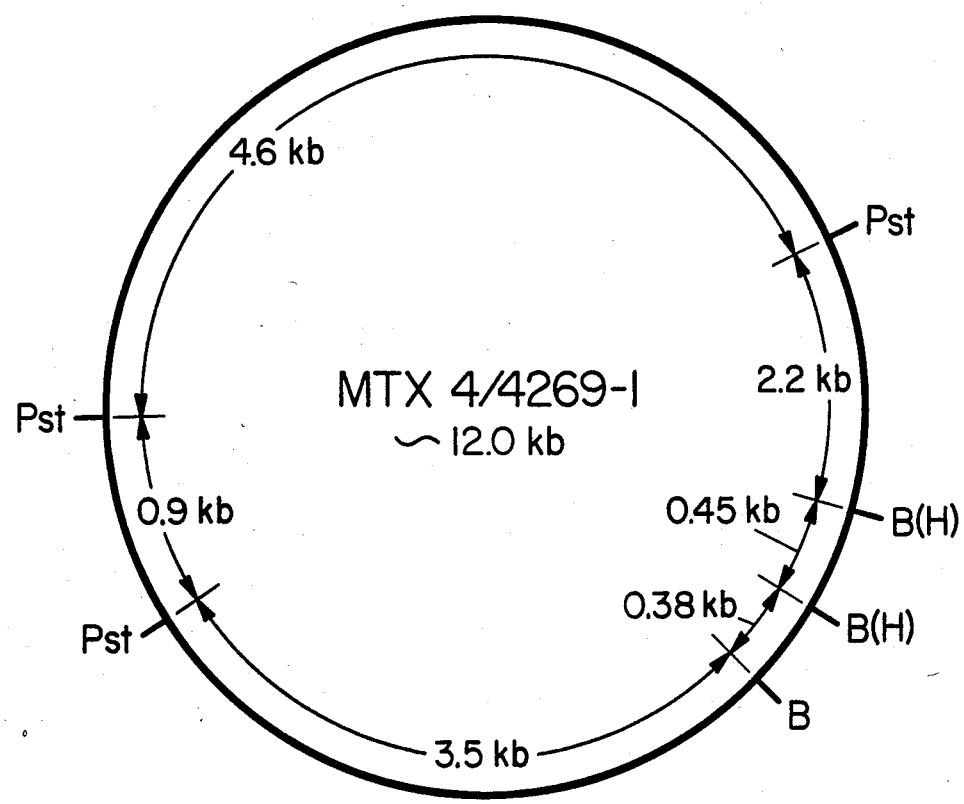
FIG. 7 is a schematic restriction map of MTX4/4269-1.

Another plasmid MTX4/4269-1 was digested in the same manner as MTX4/4269-13 and yielded 6 fragments of 4.6 kb, 3.5 kb, 0.9 kb, 2.2 kb, 0.38 kb, and 0.45 kb. FIG. 7 is a restriction map consistent with these results. The 1.5 kb fragment indicates the presence of two 480-base pair fragments tandemly inserted in the opposite orientation as the tandemly inserted 480-base pair fragments of MTX/4269-13.

Transformation of Yeast DBY-746 with MTX4/4269-5

Yeast DBY-746 was transformed using the same procedures described in Example I hereinabove except that plasmid MTX4/4269-5, MTX4, MTX5 and YEp13 were used.

Detection of YEp13, MTX4, MTX5 and MTX4/4269-5 Plasmids in Yeast

Plasmid DNA from fifty ml of yeast spheroplasts was extracted by a modified method of Birnhoim et al. The yeast cells were grown previously in minimal medium without leucine and stored at 5° C. for 20 hours and spheroplasts were obtained by a modification of the method previously described. Washed cells were resuspended in 1/20th volume 1M sorbitol, 25 mM EDTA, 50 mM dithiothreitol, pH 8.0 at 30° C. for 10 minutes. Cells were washed with sorbitol, then partially digested in 1/20th volume 1M sorbitol, 0.1M sodium citrate, pH 5.0, 10 mM EDTA and 5 ug/ml Zymolyase 60,000 (Kirin) for 20 minutes at 30° C. A clarified supernatant was obtained by centrifugation at 15,000 rpm at 0° C. for 30 minutes in a Sorvall SA-600 rotor. DNA was precipitated in ethanol, then resuspended in buffer plus 40 ug/ml RNaseI (Sigma) at 37° C. for 30 minutes. Following a second ethanol precipitation, the DNA preparations were extracted three times in phenol, once in chloroform/isoamyl alcohol (24:1), and reprecipitated in ethanol.

Plasmid DNA preparations extracted from the yeast spheroplasts were run on 0.7% agarose gel at 125 V for 1.75 hours, then transferred to nitrocellulose filter sheets for Southern hybridization. The yeast DNA filters were hybridized to probes of $^{32}$P-radiolabelled pBR327, MTX5, and the Mtx$^r$ DHFR nucleotide sequence, in separate experiments, by the dextran sulfate formamide method (Wahl et al., P.N.A.S. SA (1979) 76: 3693-3687). The radiolabeled probes were generated by nick translation methods as described above in Example I.

All four plasmids YEp13, MTX4, MTX5 and MTX4/4269-5 were detected by hybridization to $^{32}$P-labeled pBR327 probes. Relative migration of the plasmids with respect to HindIII-digested Lambda DNA used as a standard indicated that no detectable change in plasmid size occurred in the yeast cells. As expected, MTX4, MTX 5 and MTX4/4269-5 but not YEp13 were detected by hybridization with the radiolabeled Mtx$^r$-DHFR probes. Hybridization of the plasmids extracted from the transformed yeast with radiolabeled MTX5 had the same results. In addition, there was a high-mobility species in all four plasmid preparation which strongly hybridized to the MTX5 probe and was deduced to be the endogenous 2-micron section of plasmid of YEp13.

Transcriptional Expression of RNA or MTX4, MTX5, MTX4/4269-5 and YEp13 in Yeast

Yeast cells transformed with one of plasmids MTX4, MTX5, MTX4/4269-5 or YEp13 were treated as described above to form spheroplasts. The spheroplasts were lysed in a buffer containing inhibitors of nuclease activity. The lysis buffer contained 50 mM TRIS, pH 7.5, 50 mM NaCl, 10 mM EDTA, 50 mM beta-mercaptoethanol, 1% SDS and 1% diethylpyrocarbonate (DEPC). The mixtures were extracted in phenol and treated with DNAse to yield a pure sample of RNA.

Total yeast cell RNA was isolated from each of the transformed yeast lines, denatured, run on a formaldehyde-containing agarose gel, transferred to nitrocellulose filters and hybridized to the deoxynucleotide sequence coding for Mtx$^r$ DHFR labeled with $^{32}$P. Extensive hybridization to RNA of the three Mtx$^r$ DHFR clones, i.e., MTX4, MTX5 and MTX4/4269-5, was observed. Only weak hybridization between the probe and YEp13 or yeast ribosomal RNA was obtained.

Gel patterns of RNA from the four transformants were also hybridized with probes of $^{32}$P-labeled 480-base pair fragment DNA. Extensive hybridization occured only with MTX4/4269-5. In addition, discrete bands associated only with gels of MTX4/4269-5 RNA strongly hybridized to the $^{32}$P-labelled 480-base pair probe, indicating that at least portions of the 480-base pair fragment are transcribed in yeast. Experiments to determine the strand-specificity of transcription indicate that a significant amount of transcription in the 480-region is from the "correct" strand.

Cloning of the 480-Base Pair Fragment into MTX5

Preparation of MTX5 Vector DNA

MTX5 plasmids were prepared by the Birnboim-cesium chloride method described above. About 18.6 ug of MTX5 plasmid DNA was digested with 20 units of Bam HI (BRL) in 200 microliters of the approximate salts at 37° C. for 16 hours. Digestion was shown to be complete by the presence of a single 11.2 kb band on a 0.8% agarose gel. The digested MTX5 DNA was electroeluted, precipitated twice in ethanol and resuspended in 25 ul distilled water.

About 15 ul (10–12 ug) of resuspended digested MTX5 was treated with 3.3 units of calf intestine alkaline phosphatase in 30 mM TRIS-chloride pH 7.8 at 65° C. for 15 minutes to remove terminal phosphates. The mixture was extracted and precipitated as described for the MTX4 above. Phosphatase-treated MTX5 remained in the linear form, as analyzed by agarose gel electrophoresis, whereas untreated vector generated slower-migrating species under standard ligation conditions. The linear MTX5 preparation was resuspended in 15 ul of distilled water.

Preparation of the 480-Base Pair Fragment with Bam HI Linkers

About 3 ug of the 480-base pair fragment was made completely double-stranded using Klenow fragment enzyme as described previously. Approximately 5 ug of Bam HI octanucleotide linkers (Collaborative Research) were phosphorylated using unlabelled ATP. Phosphorylated Bam HI linkers were ligated to the 480-pase pair fragment as described for MTX4, except that the ligation was conducted at room temperature (20° to 22° C.) for 16 hours, then inactivated by heating at 65° C. for 10 minutes.

Thirty-five ul of the mixture containing double-stranded 480-base pair fragments and phosphorylated Bam HI linkers was supplemented with 100 mM final concentration sodium chloride and 6 units of Bam HI, then brought to a volume of 50 ul with distilled water. 480-base pair inserts having Bam HI ends were generated at 37° C. for 40 hours. Free linkers were removed by the spermine precipitation method (Hoopes, B. C. and W. R. McClure, 1981, *Nucl. Acids Res.*, 9, 5493–5504). The purified 480-base pair fragment having Bam HI ends was resuspended in 6 ul of ligase buffer. An aliquot of the fragment preparation formed multimers upon treatment with T4 ligase and ATP. Bam HI but not HindIII converted the multimers to monomers, indicating that the terminal HindIII site of the 480-base pair fragment was not reconstituted by the linkers.

Approximately 2.5 ug of the Bam HI-linked 480-base pair fragment was ligated to 5 ug of the MTX5 vector in 30 ul of ligase buffer salt, 1.0 mM ATP and 200 units of T4 ligase as described previously.

Transformation of *E. coli*

Fifteen microliters of each of the above described ligation mixtures was used to transform 200 ul of competent LE 392 *E. coli* cells. Transformants were selected on L-agar containing 10 ug/ml ampicillin.

Analysis of MTX5/4269 Clones

Figure 8:
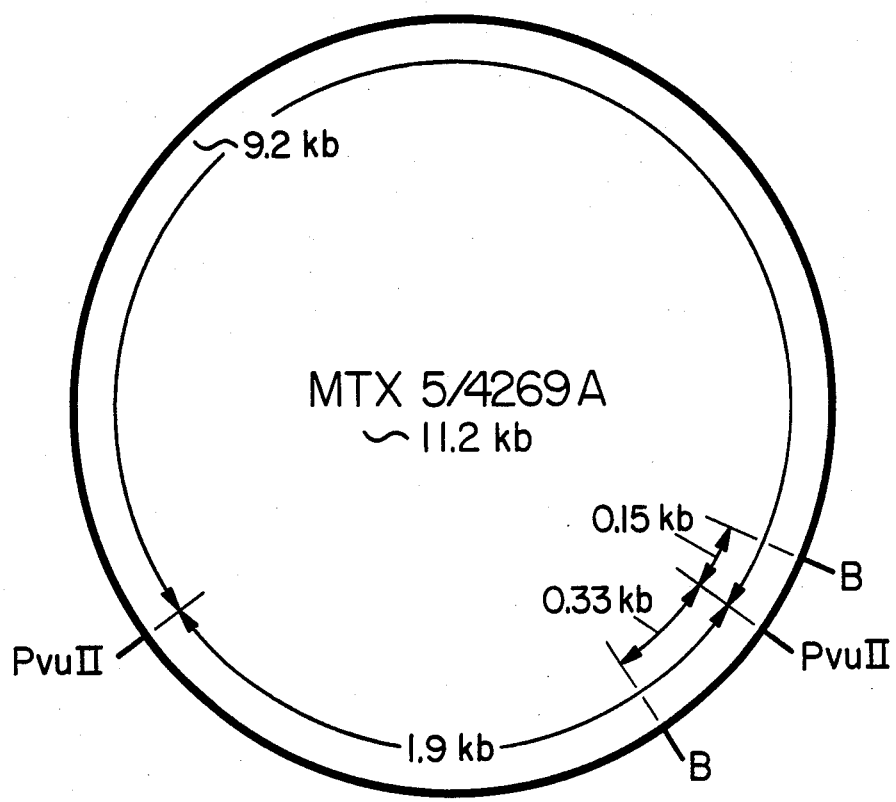
FIG. 8 is a limited restriction map of MTX5/4269A.
Figure 9:
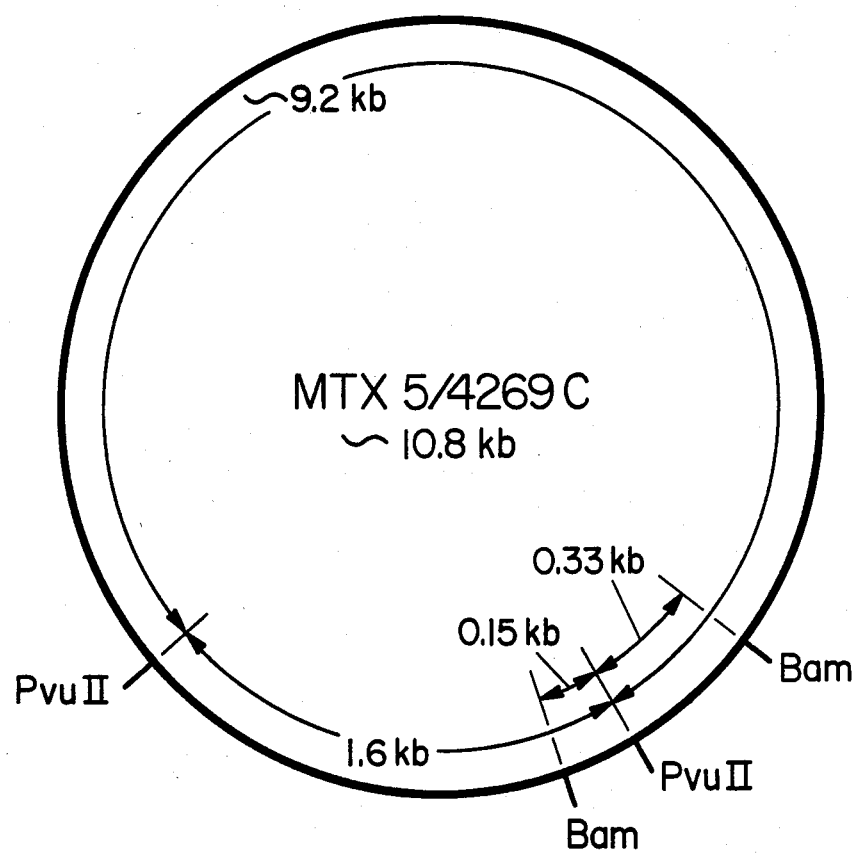
FIG. 9 is a limited restriction map of MTX5/4269C.

Plasmids from 9 ampicillin-resistant *E. coli* colonies were isolated by the Birnhoim method described before. The orientation of the 480-base pair fragment was qualitatively determined by mapping a single internal PvuII restriction site of the 480-base pair fragment relative to the PvuII site of the vector. The PvuII site of the 480-base pair fragment is about 150-base pairs from the "Bam end" of the 480-base pair fragment. Thus it was expected that one orientation of the 480-base pair fragment would yield a PvuII fragment approximately 300-base pairs larger than the PvuII fragment of the oppositely oriented 480-base pair fragment. MTX5/4269 plasmids were digested with 6 units of PvuII in HindIII buffer salts at 37° C. for 3 hours, then sized on a 1% agarose gel. Three plasmids gave digestion fragments of about 9.2 kb and about 1.9 kb, indicating that the 480-base fragment is oriented as shown in MTX5/4269A (FIG. 8). Six clones had fragments of about 9.2 kb and about 1.6 kb, indicating that the 480-base pair fragment is oriented as shown in MTX5/4269C (FIG. 9). DNA from all six colonies showed homology to the $^{32}$P-labeled 480-base pair fragment.

From the foregoing description and examples, it will be readily apparent to those skilled in the art that the above described plasmids have a more general use. Thus, although the inventors have used methotrexate-resistant dihydrofolate reductase as a marker sequence, other DNA fragments having a nucleotide sequence or sequences coding for other desired gene product or products may be used. Thus, marker sequences other than the above MTX$^r$ DHFR nucleotide sequences, may be used depending on the characteristics of the host to be transformed and the needs of the user. For example, DNA sequences conferring resistance to other substances toxic to the host, may be used. Such sequences are well known to those skilled in the art and include antibiotic resistance, heavy metal resistance, and the like. Such other markers are considered to be well within the scope of the invention. Furthermore, although the initial selectable marker sequence of YEp13 codes for ampicillin, tetracycline resistance and LEU2, another initial selectable marker or markers may be used if available in another hybrid plasmid.

It should also be apparent from the foregoing that DNA fragments having nucleotide sequences coding for the desired gene product other than marker characteristics may be used in some cases along with a marker nucleotide sequence or, in other cases, in place of a marker nucleotide sequence. In the former case, characteristics that are not easily selected such as enhanced amino acid production, may be placed into the plasmid along with or adjacent to the marker nucleotide sequence and a selection of the transformed host may be made utilizing the marker. In the latter cases, it may be desirable to place a DNA fragment having a nucleotide sequence coding for a desired gene product into the plasmid instead of the marker.

One of the particular advantages of the vector system described hereinabove is its ability to shuttle between prokaryotic and eukaryotic hosts. Thus, the vector carrying the desired nucleotide sequence, may be constructed in vivo, transformed into a prokaryotic host for replication, and amplified in the prokaryotic host relying on the short generation time of prokaryotic organisms. The thus amplified vector may then be recovered from the prokaryotic host in high copy number and used for in vitro transformation of the eukaryotic hosts. Thus, a higher number of eukaryotic transformants may be obtained in a short period of time by using the prokaryotic host to amplify the vector and using the thus amplified vector to transform the eukaroytic host.

It will further be apparent to those skilled in the art that the nucleotide sequence containing a plant promoter may be replaced by other promoters of eukaryotic or prokaryotic origin or function. The term "function" as used herein refers to promotors that although not derived from a eukaroytic cell, nevertheless act as promotors in the transcription of RNA in eukaryotic cells. Such promotors include for example promotors derived from Ti plasmids of *Agrobacterium tumefaciens*. These latter plasmids direct the synthesis of various RNAs utilizing the transcription apparatus of the host plant cell.

What is claimed is:

1. A recombinant plasmid adapted for transformation of at least one prokaryotic and one eukaryotic host, said plasmid having a nucleotide sequence a portion thereof coding for a promotor said nucleotide sequence having the base sequence:

```
        10         20         30
AAGCTTGAAAATTAAGCCCCCCCCCGAAAT
HindIII 40         50         60
CATCGCCACAGGTCGTCCCAGCCCGGCATC 70         80         90
TATATATAGCGCCAATATAGTTTGTCTTAC 100        110        120
ACAAACACACCTCACATCATGAATTTCGCA 130        140        150
GATACTCCTTGGCCTCCCTCGACCTAGACT 160        170        180
GGGCATGCGAAGAGTTTATCAAAACTTATG 190        200        210
GTGCATCTCCACAATTGGAAACAGGAGAGG 220        230        240
TAATCCAAACAAACAATGGGCTGCTGTATT 250        260        270
TGTATGGCAAAGGTTCACTCTCACAGCGGA
```

-continued

```
           280        290        300
TTCATGACAJACACCTCAAATTTAAGGAGA 310        320        330
AGGAAGGATTATCCTTCACTACCATAAAGC 340        350        360
CAGCTGAGATGAAGGCGCAACAAAGTGATT 370        380        390
TAACTTATTATGTCGCCATTTTTCAAAGCA 400        410        420
ACTATTTCCTGTGCGTTTCAAATCCAGAGA 430        440        450
AAGGCTTTCTGAGA9TGCCATAATCGCCCA 460        470        480
TTTCTGTACCCCATAGTAGCCCATGGATCC
                                 BamHI
``` wherein A is adenine, T is thymine, C is cytosine, G is guanine, J is C or G, and 9 is ambiguous base assignment which may indicate adenine.

2. The plasmid of claim 1 wherein said promotor functions as a eukaryotic promoter.

3. The plasmid of claim 1 wherein said promoter is a plant promoter.

4. The plasmid of claim 1 further including a nucleotide sequence coding for a methotrexate-resistant dihydrofolate reductase marker said nucleotide sequence being located adjacent to and upstream of the nucleotide sequence containing a portion which codes for a promoter.

5. The plasmid of claim 1 wherein said eukaryotic host is yeast and said prokaryotic host is bacterial.

6. The plasmid of claim 1 wherein said plasmid is YEp13 digested with BamHI and HindIII to yield an insertion site for said nucleotide sequence.

7. The plasmid of claim 5 further including a nucleotide sequence coding for a methotrexate-resistant dihydrofolate reductase marker said nucleotide sequence being located adjacent to and upstream of the nucleotide sequence containing a portion which codes for a promoter.

8. The plasmid of claim 6 further including a nucleotide sequence coding for a methotrexate-resistant dihydrofolate reductase marker said nucleotide sequence being located adjacent to and upstream of the nucleotide sequence containing a portion which codes for a promoter.

9. Plasmid MTX4/4269, cloned into *Escherichia coli* strain LE392 which has been deposited under ATCC designation 34395.

10. Plasmid MTX5/4269C, cloned into *Escherichia coli* strain LE392 which has been deposited under ATCC designation 39394.

* * * * *